US012600691B2

(12) United States Patent
Brammer et al.

(10) Patent No.: US 12,600,691 B2
(45) Date of Patent: Apr. 14, 2026

(54) PROCESS FOR PRODUCING MIXED ALCOHOLS FROM PURGE STREAM CONTAINING OCTENE

(71) Applicant: Dow Global Technologies LLC, Midland, MI (US)

(72) Inventors: Michael A. Brammer, Freeport, TX (US); Sean W. Ewart, Lake Jackson, TX (US); Wanglin Yu, Lake Jackson, TX (US); Bruce D. Hook, Lake Jackson, TX (US); Sally Demaio-Turner, Lake Jackson, TX (US); Sung-Yu Ku, Lake Jackson, TX (US); Yujun Liu, Lake Jackson, TX (US); Jin Liu, Freeport, TX (US); Jianping Zeng, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 609 days.

(21) Appl. No.: 17/999,993

(22) PCT Filed: May 27, 2021

(86) PCT No.: PCT/US2021/034425
§ 371 (c)(1),
(2) Date: Nov. 28, 2022

(87) PCT Pub. No.: WO2021/242962
PCT Pub. Date: Dec. 2, 2021

(65) Prior Publication Data

US 2023/0227388 A1 Jul. 20, 2023

Related U.S. Application Data

(60) Provisional application No. 63/031,965, filed on May 29, 2020.

(51) Int. Cl.
*C07C 45/50* (2006.01)
*B01J 31/18* (2006.01)
(Continued)

(52) U.S. Cl.
CPC ............ *C07C 45/50* (2013.01); *B01J 31/185* (2013.01); *C07C 29/172* (2013.01); *C07C 29/34* (2013.01); *C07C 29/74* (2013.01); *C07C 47/02* (2013.01)

(58) Field of Classification Search
None
See application file for complete search history.

(56) References Cited

U.S. PATENT DOCUMENTS 4,426,542 A 1/1984 Barker et al.
4,518,809 A * 5/1985 Forster .................. C07C 29/141 568/840

(Continued)

FOREIGN PATENT DOCUMENTS

KR 20170074658 A * 6/2017 ................ C08F 6/16

OTHER PUBLICATIONS

Chada, J. P. et al. "Oligomerization of 1-butene over carbon-supported CoOx and subsequent isomerization/hydroformylation to n-nonanal" Catalysis Communications 114 (2018) 93-97 (Year: 2018).*

(Continued)

*Primary Examiner* — Medhanit W Bahta
(74) *Attorney, Agent, or Firm* — Boyle Fredrickson S.C.

(57) ABSTRACT

The present disclosure provides a process. In an embodiment, the process includes providing a purge stream composed of octene isomers. The process includes subjecting the purge stream to hydroformylation conditions, and forming a reaction product composed of nonanals.

14 Claims, 1 Drawing Sheet

(51) Int. Cl.

| | |
|---|---|
| ***C07C 29/17*** | (2006.01) |
| ***C07C 29/34*** | (2006.01) |
| ***C07C 29/74*** | (2006.01) |
| ***C07C 47/02*** | (2006.01) |

(56) References Cited

U.S. PATENT DOCUMENTS

| | | | |
|---|---|---|---|
| 4,598,162 | A | 7/1986 | Forster et al. |
| 5,288,918 | A * | 2/1994 | Maher .................... B01J 31/185 558/71 |
| 5,741,944 | A | 4/1998 | Bryant et al. |
| 6,090,986 | A | 7/2000 | Godwin et al. |
| 6,573,414 | B2 | 6/2003 | Mcatee et al. |
| 7,652,173 | B2 | 1/2010 | Crause et al. |
| 8,211,949 | B2 | 7/2012 | Varineau et al. |
| 9,315,436 | B2 | 4/2016 | Barnes et al. |
| 9,493,726 | B2 | 11/2016 | Vinson et al. |
| 10,562,833 | B2 | 2/2020 | Fridag et al. |
| 11,214,533 | B2 | 1/2022 | Ku et al. |
| 2002/0028974 | A1* | 3/2002 | Scholz .................... C07C 29/16 568/429 |
| 2011/0098492 | A1 | 4/2011 | Varineau |
| 2015/0158805 | A1* | 6/2015 | Frey ........................ C07C 67/08 508/463 |
| 2015/0183901 | A1 | 7/2015 | Ghosh et al. |
| 2021/0387935 | A1 | 12/2021 | Brammer et al. |

OTHER PUBLICATIONS

Machine translation of Patent No. KR20170074658A, Jun. 30, 2017, pp. 1-14 (Year: 2017).*

* cited by examiner

PROCESS FOR PRODUCING MIXED ALCOHOLS FROM PURGE STREAM CONTAINING OCTENE

BACKGROUND

In the production of ethylene/octene copolymer, ethylene, octene comonomer and a polymerization catalyst are introduced into a polymerization reactor under suitable reaction conditions (in the presence of solvent and chain transfer agent) to yield an ethylene/octene copolymer polymerization product stream. The product stream is removed from the reactor and contains ethylene/octene copolymer, and hydrocarbon species of unreacted monomer (ethylene), unreacted comonomer (octene), and other associated hydrocarbons (hydrogen, ethane, methane, propane, pentane, hexane, butane). The ethylene/octene copolymer is separated from the solvent and unreacted monomer and unreacted comonomer by devolatilization. Granular ethylene/octene copolymer is subsequently collected after pelletization and cooling. After the ethylene/octene copolymer is separated from the product stream, the hydrocarbon species are either recycled back into the polymerization reactor or purged from the system.

Reclamation of the purged hydrocarbon species is one of the biggest challenges facing large-scale polyolefin production. For example, conversion of the octene comonomer in ethylene/octene copolymer polymerization production is generally very low, for example between 10 and 20%. This means that 80-90% of the octene can pass through the reactor without being converted to polymer.

Ideally, the octene comonomer is recycled back to the polymerization reactor. Although the recycle of volatile monomers, like ethylene, is very efficient, the recycle of octene is difficult, especially when other saturated hydrocarbons are present in the product stream. The boiling point of octene is very close to the boiling point of other saturated and unsaturated species present in the product stream, making octene separation difficult. The fresh octene stream also includes other isomers of octene (from 1 wt % to 5 wt % octene isomers based on total weight octene). The octene isomers typically do not react with the ethylene in the polymerization process. Consequently, the octene isomers aggregate or otherwise "build up" in the continuous recirculation of the recycle stream, diminishing the efficiency of recycle as a feed stream. In this manner the octene isomers can build up to as much as 70% of the total recycle stream.

Hence, the art recognizes the on-going need for ways to utilize purge stream hydrocarbon species that avoids mere disposal of same. A need further exists for utilizing octene monomer that is present in the purge stream.

SUMMARY

The present disclosure provides a process. In an embodiment, the process includes providing a purge stream composed of octene isomers. The process includes subjecting the purge stream to hydroformylation conditions, and forming a reaction product composed of nonanals.

DEFINITIONS

Figure 1:
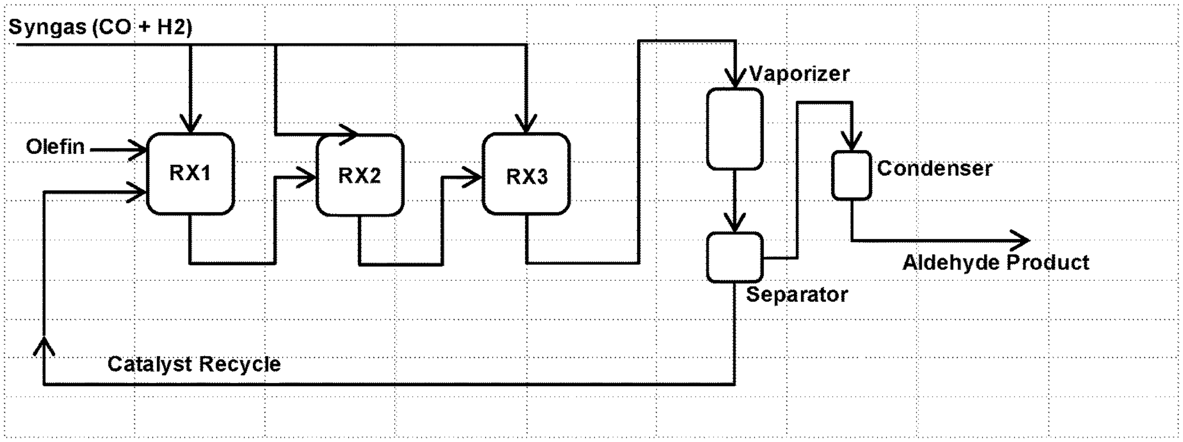
FIG. 1 is a schematic representation of a hydroformylation reactor system for providing hydroformylation conditions, in accordance with an embodiment of the present disclosure.

Any reference to the Periodic Table of Elements is that as published by CRC Press, Inc., 1990-1991. Reference to a group of elements in this table is by the new notation for numbering groups.

For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

The numerical ranges disclosed herein include all values from, and including, the lower and upper value. For ranges containing explicit values (e.g., 1 or 2, or 3 to 5, or 6, or 7), any subrange between any two explicit values is included (e.g., the range 1-7 above includes subranges of 1 to 2; 2 to 6; 5 to 7; 3 to 7; 5 to 6; etc.).

Unless stated to the contrary, implicit from the context, or customary in the art, all parts and percents are based on weight and all test methods are current as of the filing date of this disclosure.

An "alcohol" is a compound having a hydroxyl group (—OH) attached to a hydrocarbon radical.

An "aldehyde" is a compound having a carbonyl functional group (C═O) attached to one hydrocarbon radical and a hydrogen atom.

An "alkene" is a hydrocarbon containing a carbon-carbon double bond.

The terms "blend" or "polymer blend," as used herein, is a blend of two or more polymers. Such a blend may or may not be miscible (not phase separated at molecular level). Such a blend may or may not be phase separated. Such a blend may or may not contain one or more domain configurations, as determined from transmission electron spectroscopy, light scattering, x-ray scattering, and other methods known in the art.

The term "composition" refers to a mixture of materials which comprise the composition, as well as reaction products and decomposition products formed from the materials of the composition.

The terms "comprising," "including," "having" and their derivatives, are not intended to exclude the presence of any additional component, step or procedure, whether or not the same is specifically disclosed. In order to avoid any doubt, all compositions claimed through use of the term "comprising" may include any additional additive, adjuvant, or compound, whether polymeric or otherwise, unless stated to the contrary. In contrast, the term "consisting essentially of" excludes from the scope of any succeeding recitation any other component, step, or procedure, excepting those that are not essential to operability. The term "consisting of" excludes any component, step, or procedure not specifically delineated or listed. The term "or," unless stated otherwise, refers to the listed members individually as well as in any combination. Use of the singular includes use of the plural and vice versa.

An "enal" is an aldehyde compound that contains a carbon-carbon double bond. Enals may be formed by aldol (or cross-aldol) condensation of aldehydes followed by dehydration of the resulting intermediate compound. A non-limiting example of an enal is 2-ethylhexenal, which results from the self-condensation of $C_4$ aldehyde as shown below:

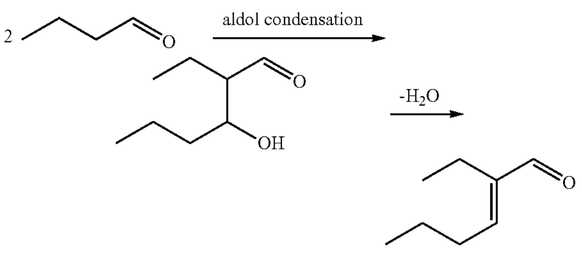

2-ethylhexenal

An "enol" is an alcohol which contains a carbon-carbon double bond. An enol may be formed by partial hydrogenation of an enal.

An "ethylene-based polymer" is a polymer that contains more than 50 weight percent (wt %) polymerized ethylene monomer (based on the total amount of polymerizable monomers) and, optionally, may contain at least one comonomer. Ethylene-based polymer includes ethylene homopolymer, and ethylene copolymer (meaning units derived from ethylene and one or more comonomers). The terms "ethylene-based polymer" and "polyethylene" may be used interchangeably.

A "hydrocarbon" is a compound containing only hydrogen atoms and carbon atoms. A "hydrocarbonyl" (or "hydrocarbonyl group") is a hydrocarbon having a valence (typically univalent).

The term "1-octene," as used herein, is an unsaturated hydrocarbon α-olefin having the molecular formula $C_8H_{16}$ and the unsaturation is at the alpha position. 1-octene has the molecular Structure (A) as shown below.

Structure (A)

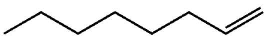

The term "isomer of octene," as used herein, is an unsaturated hydrocarbon having the molecular formula $C_8H_{16}$, and the unsaturation (the double bond) is not at the alpha position. In other words, the term "isomer of octene" is any octene to the exclusion of 1-octene. Nonlimiting examples of isomers of octene include cis-2-octene, trans-2-octene, cis-3-octene, trans-3-octene, and combinations thereof as well as cis-4-octene, trans-4-octene, branched octene isomers and combinations of thereof.

The term "linear internal octene isomer" as used herein, is a linear and unsaturated hydrocarbon composed of an eight-carbon chain, and the unsaturation (the double bond) is not at the alpha position. Linear internal octene isomers include cis-2-octene, trans-2-octene, cis-3-octene, trans-3-octene, cis-4-octene, trans-4-octene, and combinations thereof. The term "branched $C_8$ olefin" as used herein is an unsaturated hydrocarbon having the molecular formula $C_8H_{16}$, and a main chain length of 7 carbon atoms. In contrast to the linear nature of Structure A, branched $C_8$ olefins contain at least one hydrocarbon radical directly bonded to the main chain. Nonlimiting examples of branched $C_8$ olefins include methylheptenes such as 3-methyl-2-heptene, 3-methyl-3-heptene, 5-methyl-2-heptene, 5-methyl-3-heptene, and the like. Additional nonlimiting examples of branched $C_8$ olefins include dimethylhexenes such as 3,4-dimethyl-2-hexene, 3,4-dimethyl-3-hexene, 2,3-dimethyl-3-hexene and the like. Further nonlimiting examples include ethylhexenes, such as 2-ethyl-1-hexene and the like.

An "olefin" is an unsaturated, aliphatic hydrocarbon having a carbon-carbon double bond.

A "polymer" is a compound prepared by polymerizing monomers, whether of the same or a different type, that in polymerized form provide the multiple and/or repeating "units" or "mer units" that make up a polymer. The generic term polymer thus embraces the term homopolymer, usually employed to refer to polymers prepared from only one type of monomer, and the term copolymer, usually employed to refer to polymers prepared from at least two types of monomers. It also embraces all forms of copolymer, e.g., random, block, etc. The terms "ethylene/α-olefin polymer" and "octene/α-olefin polymer" are indicative of copolymer as described above prepared from polymerizing ethylene or octene respectively and one or more additional, polymerizable α-olefin monomer. It is noted that although a polymer is often referred to as being "made of" one or more specified monomers, "based on" a specified monomer or monomer type, "containing" a specified monomer content, or the like, in this context the term "monomer" is understood to be referring to the polymerized remnant of the specified monomer and not to the unpolymerized species. In general, polymers herein are referred to as being based on "units" that are the polymerized form of a corresponding monomer.

Test Methods

Gas Chromatography (GC).

The composition of the spent solvent and the hydroformylation reaction product is determined by Gas Chromatography (GC) using the following conditions:

| | |
|---|---|
| Instrument | Agilent Technologies Model 7890 with Flame Ionization Detector |
| Data System | Agilent OpenLab A.02.01 |
| Injector Inlet | 270° C. using 4 mm split/splitless liner with glass wool PN 092002 |
| Column mode: Ramped Pressure | 20 psi (hold for 10 min.) ramp at 0.5 psi/min to 30 psi (hold 1 min.) ramp at 1 psi/min to 50 psi (hold 49 min.) |
| Mode | Split |
| Split Ratio | 150:1 |
| Injection Volume | 1 μL |
| Column | Supelco Petrocol DH 100 m × 0.25 mm i.d. × 0.5 μm |
| Oven Ramp. | 40° C. (Hold 40 min.) Ramp at 10° C./min. to 220° C. (hold 5 minutes) Ramp at 5° C./min. to 260° C. (hold 19 min.) Ramp at 5° C./min. to 270° C. (hold 48 min.) |
| Run Time | 140 minutes |
| Detector | FID set at 270° C. |
| FID Hydrogen Flow | 40 mL/min. |
| FID Air Flow | 400 mL/min. |
| Nitrogen (Make-up) gas flow | 20 mL/min. |

Quantitation for the data of Table 1 (in the Examples section below) and Section A of the Examples section is based on weight percent using response factors derived from standard solutions at known concentration.

The compositions of the cross-aldol reaction product and the crude alcohol product are determined by both GC and Gas Chromatography/Mass Spectrometry (GC/MS) using the following conditions:

| | |
|---|---|
| Instrument | Agilent Technologies Model 6890 with Flame Ionization Detector and 5973 MSD |
| Data System | Agilent Enhanced Chemstation D.01.02.16 |
| Injector Inlet | 250° C. using 4 mm split/splitless liner with glass wool PN 092002 |
| Column: | Agilent VF17-MS, 30 m × 0.32 mm × 0.25 μum |
| Column mode: Constant flow | Constant Flow at 2 mL/min |
| Mode | Split |
| Split Ratio | 50:1 |
| Injection Volume | 1 μL |
| Column | Agilent VF-17MS 30 m × 0.32 m × 0.25 um |
| Oven Ramp. | 30° C. (Hold 2.20 min.) Ramp at 10° C./min. to 330° C. (hold 2 minutes) |
| Run Time | 34.20 Minutes |
| Detector | FID set at 250° C. |
| FID Hydrogen Flow | 40 mL/min. |
| FID Air Flow | 450 mL/min. |
| Nitrogen (Make-up) gas flow | 45 mL/min. |
| MSD Source Temp: | 230° C. |
| MSD Quad Temp: | 150° C. |
| MSD Tune: | STune |
| MSD Scan Parameters: | Scan 30-500 m/z |
| Library: | NIST MS Search 2.0f, build Oct. 22, 2009 |

Quantitation for Sections B-E in the Examples section is based on GC area percent from the FID signal (interchangeably referred to as "GC area," or "GC %"). Confirmation of peak identities/component structure is based on the Electron Ionization Mass Selective Detector signal matched to the National Institute of Standards and Testing library.

N:I ratio. Hydroformylation reactions of olefins with three or more carbon atoms produce a mixture of both linear and branched isomers. The term "N:I ratio," as used herein, is the ratio of linear or normal (N) aldehyde isomer to the branched or isoaldehyde (I) isomer. The N:I ratio is calculated by dividing the concentration of the normal aldehyde (wt %) by the concentration of the isoaldehyde (wt %). The weight percent concentration of each aldehyde isomer is determined by Gas Chromatography (GC).

DETAILED DESCRIPTION

The present disclosure provides a process. The process includes providing a purge stream composed of octene isomers and subjecting the purge stream to hydroformylation conditions. The process includes forming a reaction product composed of nonanals.

The present process includes providing a purge stream. The purge stream includes octene isomers. A "purge stream," as used herein, is one of several fractions separated, or otherwise recovered, from the effluent that exits a polymerization reactor after a polymerization reaction has occurred. The liquid effluent exiting the polymerization reactor contains solid (granular) polymer product, which is removed. A recycle stream is also removed from the effluent which is further processed and returned to the polymerization reactor. The purge stream is the stream that remains (i) after the polymer product has been recovered from the effluent and (ii) after the recycle stream has been separated from the effluent. The purge stream contains unreacted olefin monomer(s), including octene isomers, and other hydrocarbons utilized during the polymerization reaction. It is understood that the purge stream contains no, or substantially no, solid polymer product therein.

In an embodiment, the purge stream is effluent from a polymerization reactor in which ethylene is co-polymerized with octene. The purge stream includes unreacted octene isomers and other hydrocarbons.

In an embodiment, the purge stream includes (i) from 20 wt % to 55 wt %, or from 25 wt % to 50 wt % 1-octene, (ii) from 20 wt % to 60 wt % linear internal octene isomers, (iii) from 2 wt % to 8 wt % branched $C_8$ olefins, and (iv) from 5 wt % to 60 wt % hydrocarbon solvent, wherein weight percent is based on total weight of the purge stream. It is understood the components (i)-(iv) amount to 100 weight percent of the purge stream.

In an embodiment, the process includes removing any ethylene that may be present in the purge stream. The purge stream is sparged with nitrogen gas so no ethylene is present in the purge stream. The purge stream contains no, or substantially no, ethylene monomer, i.e., from 0 wt %, or from greater than 0 wt % to less than 0.5 wt % ethylene, based on total weight of the purge stream.

The process includes subjecting the purge stream to hydroformylation conditions. As used herein, "hydroformylation conditions," are reactor conditions (including temperature, and pressure), reaction ingredients (feeds of alkene, solvent, hydroformylation catalyst, and synthesis gas (also known as "syn gas" that is hydrogen ($H_2$) and carbon monoxide (CO) at molar ratio $H_2$:CO from 1:10 to 10:1 or 1:1), within one or more reactors that promote the bonding of a formyl group (—CH═O) and a hydrogen atom to a carbon-carbon double bond of an alkene (i.e., olefin) to produce aldehyde. Hydroformylation may be conducted in a liquid state, a gaseous state, and in a continuous process, a semi-continuous process, or a batch process and may involve a liquid recycle and/or gas recycle operation.

In an embodiment, the step of subjecting the purge stream to hydroformylation conditions includes contacting the purge stream with a hydroformylation catalyst under the hydroformylation conditions. The hydroformylation catalyst is a metal-organophosphite ligand complex catalyst. Non-limiting examples of suitable metals include rhodium (Rh), cobalt (Co), iridium (Ir), ruthenium (Ru), iron (Fe), nickel (Ni), palladium (Pd), platinum (Pt), osmium (Os) and mixtures thereof. In an embodiment, the metal is selected from rhodium, cobalt and ruthenium, or is selected as rhodium. The ligand is an organomonophosphite ligand, an organopolyphosphite ligand, or a combination thereof.

In an embodiment, the ligand is an organopolyphosphite ligand. The organopolyphosphite ligand is composed of a plurality of phosphite groups, each of which contains one trivalent phosphorus atom bonded to three hydrocarbyloxy radicals. Hydrocarbyloxy radicals that link and bridge two phosphite groups are referred to as "divalent hydrocarbyldioxy radicals." These bridging di-radicals are not limited to any particular hydrocarbyl species. On the other hand, hydrocarbyloxy radicals that are pendant from a phosphorus atom and not bridging two phosphite groups (i.e., terminal, non-bridging), are each required to consist essentially of an aryloxy radical. "Aryloxy" refers to either of two types of aryloxy radicals: (1) a monovalent aryl radical bonded to a single ether linkage, as in —O-aryl, wherein the aryl group comprises a single aromatic ring or multiple aromatic rings that are fused together, directly linked, or indirectly linked (such that different aromatic groups are bound to a common group such as a methylene or ethylene moiety), or (2) a divalent arylene radical bonded to two ether linkages, as in —O-arylene-O— or —O-arylene-arylene-O—, in which the arylene group includes a divalent hydrocarbon radical having a single aromatic ring or multiple aromatic rings that are fused together, directly linked, or indirectly linked (such that the different aromatic groups are bound to a common group such as a methylene or ethylene moiety). In an embodiment, aryloxy groups contain one aromatic ring or from 2 to 4 fused or linked aromatic rings, having from 5 to 20 carbon atoms, for example, phenoxy, naphthyloxy, or biphenoxy, as well as arylenedioxy radicals, such as, phenylenedioxy, naphthylenedioxy, and biphenylenedioxy. Any of these radicals and groups may be unsubstituted or substituted.

In an embodiment, the organopolyphosphite ligand includes two, three or higher numbers of phosphite groups. Mixtures of such ligands may be employed if desired. Achiral organopolyphosphites are preferred. Representative organopolyphosphites include those of formula (I):

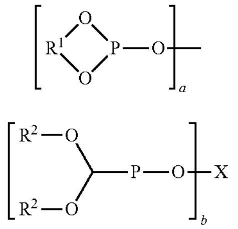

(I)

wherein X represents a substituted or unsubstituted n-valent organic bridging radical containing from 2 to 40 carbon atoms, each $R^1$ is the same or different and represents a divalent organic radical containing from 4 to 40 carbon atoms, each $R^2$ is the same or different and represents a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. Of course it is to be understood that when a has a value of 2 or more, each $R^1$ radical may be the same or different, and when b has a value of 1 or more, each $R^2$ radical may be the same or different.

In an embodiment the ligand is [[3,3',5,5'-tetrakis(1,1-dimethylethyl)-[1,1'-biphenyl]-2,2'-diyl]bis(oxy)]bis-dibenzo[d,f][1,3,2]-dioxaphosphepin having the formula of Ligand A shown below:

Ligand A

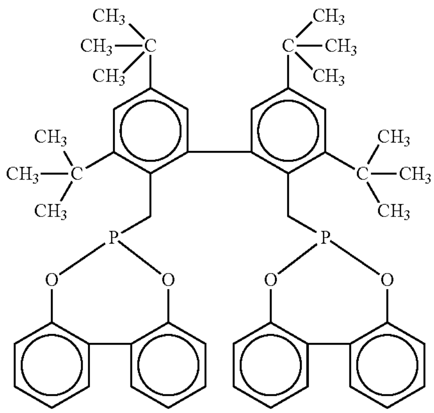

Subjecting the purge stream to the hydroformylation conditions occurs by way of a hydroformylation process. The hydroformylation process includes feeding the purge stream along with the syn gas (carbon monoxide and hydrogen) and the hydroformylation catalyst into a multi-reactor system coupled in series, i.e., the output of the first reaction zone is fed as input to the subsequent reaction zones.

The $H_2$:CO molar ratio of gaseous hydrogen to carbon monoxide ranges 1:10 to 10:1. The hydroformylation process is conducted at a reaction temperature from 50° C. to 100° C., the total gas pressure composed of purge stream, carbon monoxide, and hydrogen, ranges from 1 psia (6.9 kPa) to 2,000 psia (13,800 kPa).

Inert solvent can be employed as a hydroformylation reaction medium diluent. A variety of solvents can be used including ketones such as acetone, methyl ethyl ketone, methyl isobutyl ketone, acetophenone, and cyclohexanone; aromatics such as benzene, toluene and xylenes; halogenated aromatics including o-dichlorobenzene; ethers such as tetrahydrofuran, dimethoxyethane and dioxane; halogenated paraffins including methylene chloride; paraffinic hydrocarbons such as heptane; and the like. In an embodiment, the solvent is the aldehyde product and/or the oligomers of the aldehyde product, along with the reactive olefin or olefins.

In an embodiment, the hydroformylation process is carried out in a continuous manner in a multi-stage reactor designed with internal, physical barriers that create more than one theoretical reactive stage or zone per vessel. The hydroformylation process includes: (a) hydroformylating the purge stream with carbon monoxide and hydrogen in a liquid homogeneous reaction mixture including a solvent, and the hydroformylation catalyst; (b) maintaining reaction temperature and pressure conditions favorable to the hydroformylation of the purge stream; (c) supplying make-up quantities of the purge stream, carbon monoxide and hydrogen to the reaction medium as those reactants are used up; and (d) recovering the desired aldehyde hydroformylation product(s).

The continuous hydroformylation process can be carried out in a single pass mode in which a vaporous mixture includes unreacted purge stream and vaporized aldehyde product is removed from the liquid reaction mixture from whence the aldehyde product is recovered and make-up olefinic starting material(s), carbon monoxide and hydrogen are supplied to the liquid reaction medium for the next single pass without recycling the unreacted olefinic starting material(s).

Subjecting the purge stream to the foregoing hydroformylation conditions forms a reaction product composed of nonanals. As the purge stream contains octene isomers, subjecting the purge stream to hydroformylation conditions forms a reaction product composed of nonanals. A "nonanal" is an aldehyde containing nine carbon atoms. The purge stream is a mixture of alkenes (primarily 1-octene and octene isomers) and alkanes, consequently the reaction product from the hydroformylation reaction includes other components in addition to the nonanals. Nonlimiting examples of other components in the hydroformylation reaction product include $C_8$ olefins, $C_7$-$C_9$ alkanes, and combinations thereof.

The process includes adding an aldehyde selected from $C_4$ aldehyde, $C_5$ aldehyde, and combinations thereof (hereafter "$C_4$/$C_5$ aldehyde") to the reaction product composed of nonanals (hereafter "nonanal product") to form a mixture, mixture A. The process includes cross-aldol condensing mixture A and forming a cross-aldol product. The cross-aldol product is composed of a component selected from $C_8$ enals, $C_{10}$ enals, $C_{13}$ enals, $C_{14}$ enals, $C_{18}$ enals, and combinations thereof. The cross-aldol product may also include alcohol, solvent, water, unreacted aldehyde, and combinations thereof.

The cross-aldol condensing step includes combining the nonanal product and the $C_4$/$C_5$ aldehyde with an inorganic base catalyst, an alcohol and optionally water to form a reaction mixture, mixture A. Nonlimiting examples of suitable inorganic base catalysts include sodium hydroxide, potassium hydroxide, and combinations thereof. A nonlimiting example of a suitable alcohol is isopropyl alcohol. The reaction mixture A is heated to a temperature from 30° C. to 100° C., whereby the inorganic base catalyzes the aldol condensation reaction to form the cross-aldol product and water by-product.

In an embodiment, the process includes adding $C_4$ aldehyde, and adding the nonanals product to an inorganic base catalyst (such as sodium hydroxide) and alcohol (such as isopropyl alcohol) to form a reaction mixture, mixture A4. The process includes heating the reaction mixture A4 to a temperature from 30° C. to 100° C., or to a temperature from 40° C. to 70° C., or to a temperature from 50° C. to 60° C. whereby the inorganic base catalyzes the aldehyde-alcohol condensation and forms a cross-aldol product composed of enals selected from $C_8$ enals, $C_{13}$ enals, $C_{18}$, and combinations thereof. The cross-aldol product may further include the alcohol solvent, water, unreacted aldehydes, other $C_8$, $C_{13}$, and $C_{18}$ species (in addition to the aforementioned enals), and combinations thereof. In an embodiment, the cross-aldol product includes a majority amount of $C_8$ enals, $C_{13}$ enals, and $C_{18}$ enals wherein "majority amount" is greater than 50% of the total GC area for the cross-aldol reaction product.

In an embodiment, the process includes adding $C_5$ aldehyde, and adding the nonanals product to an inorganic base catalyst (such as sodium hydroxide) and alcohol (such as isopropyl alcohol) to form a reaction mixture, mixture A5. The process includes heating the reaction mixture A5 to a temperature from 30° C. to 100° C., or to a temperature from 40° C. to 70° C., or to a temperature from 50° C. to 60° C. whereby the inorganic base catalyzes the aldehyde-alcohol condensation and forms a cross-aldol product composed $C_{10}$ enals, $C_{14}$ enals, $C_{18}$ enals, and combinations thereof. The cross-aldol product may further include the alcohol solvent, water, optionally unreacted aldehydes and other $C_{10}$, $C_{14}$, $C_{18}$ species (in addition to the aforementioned enals). In an embodiment, the cross-aldol product includes a majority amount of $C_{10}$ enals, $C_{14}$ enals, and $C_{18}$ enals, wherein "majority amount" is greater than 50% of the total GC area for the cross-aldol reaction product.

The process includes hydrogenating the cross-aldol product. The cross-aldol product includes $C_8$ enals, $C_{10}$ enals, $C_{13}$ enals, $C_{14}$ enals, $C_{18}$ enals, and combinations thereof. The process includes forming a crude alcohol product. The crude alcohol product is composed of $C_8$ alcohols, $C_{10}$ alcohols, $C_{13}$ alcohols, $C_{14}$ alcohols, $C_{18}$ alcohols, and combinations thereof. The crude alcohol product also includes an alkane component and other $C_8$, $C_{10}$, $C_{13}$, $C_{14}$, $C_{18}$ species. In an embodiment, the crude alcohol product includes a majority amount of $C_8$ alcohols, $C_{10}$ alcohols, $C_{13}$ alcohols, $C_{14}$ alcohols, and $C_{18}$ alcohols, wherein "majority amount" is greater than 50% of the total GC area for the crude alcohol product.

In an embodiment, the hydrogenation of the cross-aldol product is conducted under liquid phase hydrogenation conditions using a heterogeneous supported metal catalyst (nickel, palladium, copper, cobalt, and/or or platinum). The liquid hourly space velocity (LHSV) of the cross-aldol product is from 0.1 hour$^{-1}$ (hr$^{-1}$) to 8 hr$^{-1}$, or from 0.5 hr$^{-1}$ to 3 hr$^{-1}$. The gas hourly space velocity (GHSV) for hydrogen is from 50 hr$^{-1}$ to 10,000 hr$^{-1}$, or from 200 hr$^{-1}$ to 4,000 hr$^{-1}$. The hydrogenation process is conducted at a reaction temperature from 100° C. to 200° C., or from 120° C. to 180° C., and under a reaction pressure from 300 psig to 1,500 psig, or from 400 psig to 1,000 psig.

In an embodiment, the process includes hydrogenating the cross-aldol product composed of $C_8$ enals, $C_{13}$ enals, $C_{18}$ enals, and combinations thereof. The process includes forming a crude alcohol product composed of $C_8$ alcohols, $C_{13}$ alcohols, $C_{18}$ alcohols, and combinations thereof. The crude alcohol product also includes an alkane component and other $C_8$, $C_{13}$, $C_{18}$ species. In a further embodiment, the process includes separating the alkane component and other species to leave a bottoms product composed of $C_8$ alcohols, $C_{13}$ alcohols, $C_{18}$ alcohols, and combinations thereof. In another embodiment, the bottoms product is further refined (e.g., via distillation) to provide fractions composed of one or more of 2-ethylhexanol, $C_{13}$ alcohol, and $C_{18}$ alcohol.

In an embodiment, the process includes hydrogenating the cross-aldol product composed of $C_{10}$ enals, $C_{14}$ enals, $C_{18}$ enals, and combinations thereof. The process includes forming a crude alcohol product composed of $C_{10}$ alcohols, $C_{14}$ alcohols, $C_{18}$ alcohols, and combinations thereof. The crude alcohol product also includes an alkane component and other $C_{10}$, $C_{14}$, $C_{18}$ species. In a further embodiment, the process includes separating the alkane component to leave a bottoms product composed of $C_{10}$ alcohols, $C_{14}$ alcohols, $C_{18}$ alcohols, and combinations thereof. In another embodiment, the bottoms product is further refined (e.g., via distillation) to provide fractions composed of one or more of 2-propylheptanol, $C_{14}$ alcohols, and $C_{18}$ alcohol.

By way of example, and not limitation, some embodiments of the present disclosure will now be described in detail in the following Examples.

EXAMPLES

The composition of purge stream recovered from an ethylene/octene polymerization production process is provided in Table 1 below. Weight percent is based on total weight of the purge stream.

TABLE 1

| Purge stream | (wt %) |
|---|---|
| hydrocarbon solvent | 6.1 |
| branched $C_9$ olefins | 4.8 |
| 1-octene | 42.4 |
| trans-4-octene | 2.4 |
| trans-3-octene and cis-4-octene (co-elution) | 9.9 |
| cis-3-octene | 2.0 |
| octane | 0.6 |
| trans-2-octene | 17.0 |
| cis-2-octene | 14.8 |

The ligand for the hydroformylation catalyst used in the inventive examples (IE) is provided in Table 2 below.

TABLE 2

| Ligand A for hydroformylation catalyst |
|---|
| 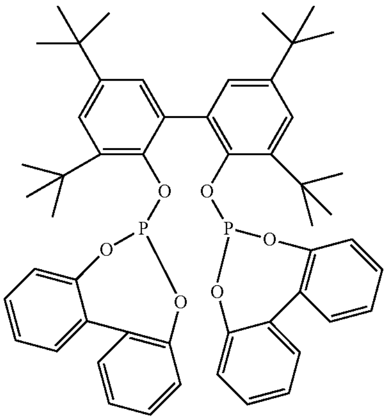 [SMILES: CC(C)(C)c1cc(-c2cc(C(C)(C)C)cc(C(C)(C)C)c2Op2oc3ccccc3c3ccccc3o2)c(Op2oc3ccccc3c3ccccc3o2)c(C(C)(C)C)c1] |
| 6,6'-[[3,3',5,5'-tetrakis(I, 1-dimethylethyl)-[1,1'-biphenyl]-2, 2'-diyl]bis(oxy)]bis-dibenzo[d,f] [1,3,2]-dioxaphosphepin |

A. Subjecting Purge Stream to Hydroformylation Conditions

Hydroformylation conditions are provided in a reactor system as shown in FIG. 1. The reactor system consists of three 1-liter stainless steel stirred tank reactors (Rx 1, Rx 2, Rx 3) connected in series. Each reactor is equipped with a vertically mounted agitator and a circular tubular sparger near the bottom for feeding the olefin and/or syngas to the reactor. The sparger contains a plurality of holes of sufficient size to provide the desired gas flow into the liquid body. Each reactor has a silicone oil shell as a way to control reactor temperature. Reactors 1 to 2 and reactors 2 to 3 are further connected via lines to transfer any unreacted gases and to allow a portion of the liquid solution containing aldehyde product and catalyst to flow (e.g., via pressure differential or by pumping) from reactor 1 to reactor 2 and from reactor 2 to reactor 3. Hence, the unreacted olefin of reactor 1 is further hydroformylated in reactor 2 and subsequently in reactor 3. In an alternate configuration, Reactor 3 (Rx 3) may be bypassed, such that only two reactors are employed.

Each reactor also contains a pneumatic liquid level controller for maintaining the desired liquid levels in the reactors. Reactor 1 further contains a line for introducing olefin, carbon monoxide and hydrogen through the sparger while makeup carbon monoxide and hydrogen are passed to reactors 2 and 3 via a transfer line that also carries the unreacted gases from reactor 1 to reactor 2 and from reactor 2 to reactor 3. Each reactor also includes a blow-off vent for controlled removal of unreacted gases if desired. A portion of the liquid reaction solution is continuously pumped from the final reactor in series to a vaporizer, which consists of a heated zone wherein a stream of flowing gas (strip gas) is utilized to sweep a portion of the volatile components to a water-cooled condenser where they can be collected as a liquid in a product receiver (crude product). The non-volatiles are passed through an aqueous extraction zone which consists of a contacting region and a separation zone. The purpose of the aqueous extraction is to extract acidic byproducts, thereby preventing additional hydrolysis of the phosphite ligands, as described in U.S. Pat. No. 5,741,944. Following the aqueous extraction, the organic non-volatiles are pumped through a recycle line back into reactor 1.

A purge stream is introduced into Reactor 1 ("olefin" in FIG. 1 represents the purge stream). The purge stream is from an ethylene-octene polymerization production process. The composition of the purge stream is provided in Table 1, above.

The hydroformylation reaction (i.e., the subjection of the purge stream to hydroformylation conditions) is conducted using two Reactors (Rx 1 and Rx 2 with Rx 3 being by-passed). Two-liters of catalyst solution composed of rhodium dicarbonyl acetylacetonate (394 ppm rhodium), ligand A (Table 2 above) (0.7 wt. %; 2.0 mole equivalents ligand A per mole rhodium), tetraethylene glycol dimethyl ether (about 15% by weight) and mixed $C_4$ aldehyde (about 85% by weight:n-butyraldehyde to iso-butyraldehyde ratio of about 30:1 based on total weight $C_4$ aldehyde) is charged to the reactor system shown in FIG. 1. The reactors are then heated to 70° C. under flowing syn gas ($H_2$:CO ratio=1:1). Reactor 1 and reactor 2 pressures are maintained at 244 psig and 220 psig respectively. The spent solvent is fed to Reactor 1 at a rate of 138 grams per hour. The vaporizer system is operated with a strip gas composed of 1:1 syn gas at a flow rate of 790 sLph; the vaporizer pressure is maintained at 7 psig with a catalyst temperature of 101° C.

After several days of continuous operation, the butyraldehydes and tetraethylene glycol dimethyl ether are removed overhead leaving a reactor process fluid composed of nonanals, aldehyde heavies (byproducts of in situ aldol condensation), unreacted olefins and hydrocarbon solvent (continually introduced as part of the spent solvent). The reaction product composed of nonanals (nonanals reaction product) is collected at a rate of 155 grams/hour. The composition of the purge stream hydroformylation reaction product (interchangeably referred to as "nonanals product") is shown in Table 3 below.

TABLE 3

Composition of nonanals product. Weight percent in Table 3 is based on total weight of the nonanals product. nonanals product

| | wt. % |
|---|---|
| $C_9$ aldehydes | 64.8 |
| unreacted $C_8$ olefins | 32.8 |
| hydrocarbon solvent | 2.4 |
| N:I ratio of the nonanals reaction product | 13.8:1 (93.2% n-nonanal |

B. Cross-Aldol Condensation

A solution of isopropanol (IPA: 37.5 g), water (4.7 g) and NaOH (1.2 g) is charged to a 300 mL Parr reactor, purged with nitrogen three times, and sealed. The solution is heated to 60° C. with vigorous stirring. A mixture of (i) $C_4$ aldehydes (25.2 g; 0.35 mol) and (ii) nonanals product (Table 3 above) (38.2 g; 0.175 mol n-nonanal) is introduced to the Parr reactor with a small lab pump at a feed rate of 40 mL/min. After addition, the temperature is maintained at 60° C. with stirring for 1 hour, completing the cross-aldol condensation reaction and forming a cross-aldol product composed of $C_8$ enals, $C_{13}$ enals, $C_{18}$ enals, and other species. The cross-aldol product is then cooled to 40° C. and quenched with 0.9 equivalents of acetic acid.

The cross-aldol product is transferred to a separatory funnel and allowed to separate for 30 minutes. A small aqueous phase (bottom phase) is removed. The cross-aldol condensation reaction (described in the paragraph above) is repeated three times and the combined organic phases (320.5 g) are concentrated on a rotary evaporator at 50° C. and 146 mbar. The residue (208 g) is washed with water (104 g) leaving an organic phase with a water content of 3.58 wt. %. Additional IPA (60 g) is added to the organic phase to facilitate azeotropic removal of water. The mixture is concentrated on a rotary evaporator a second time at 50° C. and 146 mbar to yield cross-aldol product (187.8 g); the composition of the cross-aldol product is shown in Table 4 below.

TABLE 4

Composition of cross-aldol product.

| Component | Cross-aldol product (GC %) |
|---|---|
| Isopropanol | 2.69 |
| $C_4$ aldehyde | 1.5 |
| Octenes | 4.87 |
| $C_8$ enal | 24.95 |
| $C_9$ aldehyde | 3.03 |
| $C_{13}$ enal | 15.82 |
| $C_{13}$ enal | 20.67 |
| $C_{18}$ alcohol | 0.68 |
| $C_{18}$ enal | 6.76 |
| Total unknowns | 19.03 |

Conversions of the $C_4$ aldehyde and crude $C_9$ aldehyde product are 97.2 and 93.5% respectively.

C. Hydrogenation of Cross-Aldol Product (Continuous)

The hydrogenation reaction is conducted in a tube reactor including an 8-inch piece of ⅜" stainless steel tubing packed with 8 ml of Ni-3288 that was activated with hydrogen. Ni-3288 is a hydrogenation fixed bed catalyst composed of 60 wt % nickel containing trilobe extrudate, available from BASF. The cross-aldol product (from Table 4) is mixed with hydrogen and is pumped through the Ni-3288 catalyst bed as a hydrogen-saturated liquid phase. The hydrogenation reaction is conducted at 140° C. and 500 psig, with a liquid hourly space velocity (LHSV) of 2.2 $hr^{-1}$ and gas hourly space velocity (GHSV) of 600 $hr^{-1}$ to produce the mixed alcohol/alkane product. The crude mixed alcohol/alkane product is collected in a chilled catch pot. The feed and mixed alcohol/alkane product compositions are shown in Table 5 below.

TABLE 5

Cross aldol product (feed) and crude alcohol product from continuous hydrogenation. The data in Table 5 shows effective single-pass conversion of the aldehydes to alcohols in a continuous hydrogenation process.

| Component | Feed to hydrogenation Cross-aldol product (GC area %) | Crude alcohol product |
|---|---|---|
| Isopropanol | 2.69 | 3.00 |
| $C_4$ aldehyde | 1.50 | 0.32 |
| Octenes | 4.87 | 0.00 |
| Octane | 0.00 | 4.37 |
| $C_8$ enal | 24.95 | 0.00 |
| 2-ethylhexanol | 0.00 | 27.28 |
| $C_9$ aldehyde | 3.03 | 1.28 |
| $C_{13}$ enal | 15.82 | 1.01 |
| $C_{13}$ alcohol | 0.00 | 16.00 |
| $C_{13}$ enal | 20.67 | 1.53 |
| $C_{13}$ alcohol | 0.00 | 20.38 |
| $C_{18}$ enal | 6.76 | 0.66 |
| $C_{18}$ alcohol | 0.68 | 7.32 |
| Total unknowns | 19.03 | 16.85 |

D. Separation of $C_8$-$C_{18}$ Alcohol Mixture

The crude alcohol product from Table 5 (700 g) is loaded into a 1-L round bottom distillation kettle fitted with a heating mantle and connected to a spinning band distillation column. A magnetic stir bar is used to achieve good mixing and even boiling. To remove the Lights fraction (wherein "Lights" interchangeably refers to $C_1$-$C_7$ species) from the mixed alcohol/alkane product, the column pressure is set to 100 mmHg and a reflux ratio of 8:1 is established. The temperature of liquid in the kettle ranges from 59.7° C. (onset of distillation) to 154.9° C. (Lights cut complete); the overhead vapor temperature ranges from 34.4° C. to 56.4° C. during this same time period. A Lights fraction (78.2 g) is collected as the overhead distillate leaving a $C_8$-$C_{18}$ alcohol mixture (621.0 g) as a bottoms product. The compositions of the Lights fraction and the $C_8$-$C_{18}$ alcohol mixture are shown in Table 6 below.

TABLE 6

Composition of Lights Fraction and Bottom Mixture

| Component | Lights Fraction (GC %) | Bottom Mixture (GC %) |
|---|---|---|
| Isopropanol | 17.09 | 0.00 |
| mixed alkanes | 11.25 | 0.00 |
| Octane | 53.35 | 0.00 |
| $C_8$ Aldehyde | 1.39 | 0.16 |
| 2EH | 12.05 | 26.16 |
| $C_{13}$ Alcohol | 0.00 | 18.83 |
| $C_{13}$ Alcohol | 0.00 | 22.66 |
| $C_{18}$ Alcohol | 0.00 | 11.20 |
| Total unknowns | 4.82 | 19.67 |

E. Separation of 2EH, $C_{13}$, $C_{18}$ from Bottom Mixture

Figure 2:
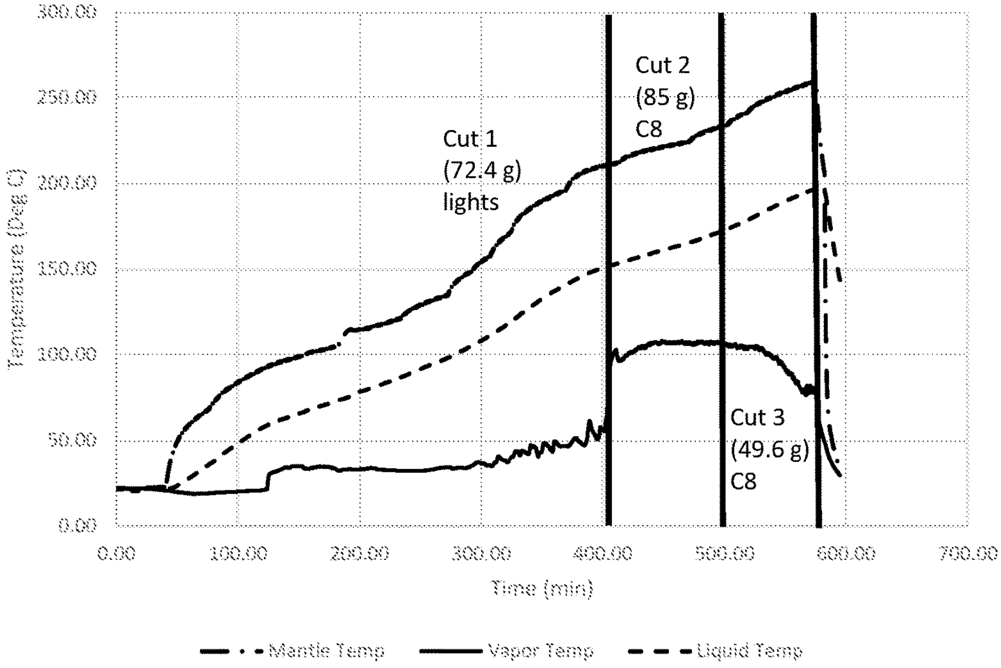
FIG. 2 is a temperature-time graph of overhead distillate separation in accordance with an embodiment of the present disclosure.

The Bottom Mixture from Table 6 (703 g) is loaded into the 1-L kettle of the spinning band distillation apparatus. The Lights fraction is removed using the distillation procedure described in Section D, above. As the temperature of the overhead vapor rises (Vapor Temperature in FIG. 2), 2-ethylhexanol (2-EH) begins to collect overhead. Three 2-ethylhexanol (2EH) cuts are taken, after which the distillation pressure is lowered to 20 mm Hg to allow three $C_{13}$ cuts to be collected. The reflux ratio is maintained throughout at 8:1. Two additional cuts are taken to further concentrate the $C_{18}$ fraction in the kettle (see Table 7 below).

TABLE 7 alcohol separation from Bottoms Product

| Major Component | Cut | Area (GC %) | Weight(g) |
|---|---|---|---|
| Lights | 1 | 86 | 72.4 |
| 2EH | 2 | 92 | 85.0 |
| | 3 | 95 | 49.6 |
| $C_{13}$ | 5 | 68 | 86.2 |
| | 6 | 87 | 89.0 |
| | 7 | 75 | 69.6 |
| $C_{18}$ | Bottom | 30 | 187.8 |

Both the overhead vapor temperature and the kettle liquid temperature are closely monitored and are used as the basis for collecting distillate cuts. The 2EH purity ranges from 92 to 95% and the $C_{13}$ product purity ranges from 67-88%.

The collected fractions may be further refined via distillation if desired.

It is specifically intended that the present disclosure not be limited to the embodiments and illustrations contained herein, but include modified forms of those embodiments including portions of the embodiments and combinations of elements of different embodiments as come within the scope of the following claims.

The invention claimed is:

1. A process comprising:

providing a purge stream comprising from 20 wt % to 55 wt % 1-octene, from 20 wt % to 60 wt % linear internal octene isomers, from 2 wt % to 8 wt % branched $C_8$ olefins, and from 5 wt % to 60 wt % solvent, wherein weight percent is based on total weight of the purge stream;

subjecting the purge stream to hydroformylation conditions; and forming a reaction product comprising nonanals.

2. The process of claim 1 wherein the subjecting comprises contacting the purge stream with a hydroformylation catalyst under hydroformylation conditions, the hydroformylation catalyst comprising a metal and an organophosphite ligand.

3. The process of claim 1 comprising adding an aldehyde selected from the group consisting of $C_4$ aldehyde, $C_5$ aldehyde, and combinations thereof to the reaction product comprising nonanals (nonanals product) to form a mixture A, mixture A comprising (i) the aldehyde, and (ii) the nonanals product;

introducing an inorganic base catalyst to mixture A;

heating mixture A and cross-aldol condensing mixture A; and forming a cross-aldol product comprising a component selected from the group consisting of $C_8$ enals, $C_{10}$ enals, $C_{13}$ enals, $C_{14}$ enals, and $C_{18}$ enals and combinations thereof.

4. The process of claim 3 comprising adding $C_4$ aldehyde to the nonanals product to form a mixture A4, mixture A4 comprising the $C_4$ aldehyde and the nonanals product;

introducing an inorganic base catalyst to mixture A4;

heating mixture A4 and cross-aldol condensing mixture A4; and forming a cross-aldol product comprising a component selected from the group consisting of $C_8$ enals, $C_{13}$ enals, $C_{18}$ enals, and combinations thereof.

5. The process of claim 3 comprising adding $C_5$ aldehyde to the nonanals product to form a mixture A5, mixture A5 comprising the $C_5$ aldehyde and the nonanals product;

introducing an inorganic base catalyst to mixture A5;

heating mixture A5 and cross-aldol condensing mixture A5; and forming a cross-aldol product comprising a component selected from the group consisting of $C_{10}$ enals, $C_{14}$ enals, $C_{18}$ enals, and combinations thereof.

6. The process of claim 4 wherein the inorganic base catalyst is selected from the group consisting of sodium hydroxide, potassium hydroxide, and combinations thereof.

7. The process of claim 4 comprising hydrogenating the cross-aldol product; and forming a crude alcohol product.

8. The process of claim 7 comprising hydrogenating a cross-aldol product comprising a component selected from the group consisting of $C_8$ enals, $C_{13}$ enals, $C_{18}$ enals, and combinations thereof; and forming a crude alcohol product comprising a component selected from the group consisting of $C_8$ alcohols, $C_{13}$ alcohols, $C_{18}$ alcohols, and combinations thereof.

9. The process of claim 8 comprising separating, from the crude alcohol product, an alcohol selected from the group consisting of 2-ethylhexanol, $C_{13}$ alcohol, $C_{18}$ alcohol, and combinations thereof.

10. The process of claim 5 comprising hydrogenating a cross-aldol product comprising a component selected from the group consisting of $C_{10}$ enals, $C_{14}$ enals, $C_{18}$ enals, and combinations thereof; and forming a crude alcohol product comprising a component selected from the group consisting of $C_{10}$ alcohols, $C_{14}$ alcohols, $C_{18}$ alcohols, and combinations thereof.

11. The process of claim 10 comprising separating, from the crude alcohol product, an alcohol selected from the group consisting of 2-propylheptanol, $C_{14}$ alcohol, $C_{18}$ alcohol, and combinations thereof.

12. A process comprising:

providing a purge stream comprising from 20 wt % to 55 wt % 1-octene, from 20 wt % to 60 wt % linear internal octene isomers, from 2 wt % to 8 wt % branched $C_8$ olefins, and from 5 wt % to 60 wt % solvent, wherein weight percent is based on total weight of the purge stream;

contacting the purge stream with a hydroformylation catalyst under hydroformylation conditions, the hydroformylation catalyst comprising a metal and an organophosphite ligand having the Structure A Structure A

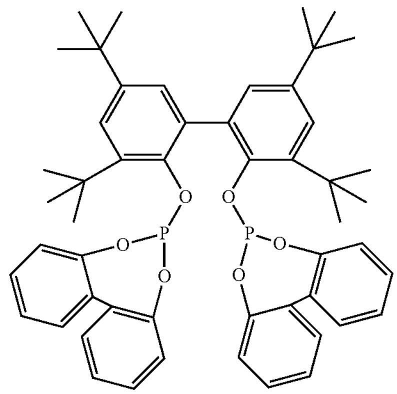

;

and forming a reaction product comprising nonanals.

13. The process of claim 12 wherein the metal is selected from group consisting of rhodium, cobalt, iridium, ruthenium, iron, nickel, palladium, platinum, osmium, and mixtures thereof.

14. The process of claim 13 wherein the metal is rhodium.

* * * * *